United States Patent
Lipinski et al.

(10) Patent No.: US 11,141,367 B2
(45) Date of Patent: Oct. 12, 2021

(54) COSMETIC COMPOSITION COMPRISING TWO OPTICAL BRIGHTENERS, METHOD, USE, AND KIT-OF-PARTS THEREOF

(71) Applicant: KAO GERMANY GMBH, Darmstadt (DE)

(72) Inventors: Normen Lipinski, Darmstadt (DE); Andreas Picker, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 904 days.

(21) Appl. No.: 15/787,952

(22) Filed: Oct. 19, 2017

(65) Prior Publication Data

US 2018/0104168 A1 Apr. 19, 2018

(30) Foreign Application Priority Data

Oct. 19, 2016 (EP) .................................... 16194498

(51) Int. Cl.

| | |
|---|---|
| *A61Q 5/02* | (2006.01) |
| *A61Q 5/04* | (2006.01) |
| *A61Q 5/12* | (2006.01) |
| *A61K 8/46* | (2006.01) |
| *A61K 8/9789* | (2017.01) |
| *A61K 8/34* | (2006.01) |
| *A61K 8/898* | (2006.01) |
| *A61Q 5/00* | (2006.01) |
| *A61K 8/97* | (2017.01) |
| *A61Q 5/06* | (2006.01) |

(52) U.S. Cl.
CPC .............. *A61K 8/466* (2013.01); *A61K 8/345* (2013.01); *A61K 8/898* (2013.01); *A61K 8/97* (2013.01); *A61K 8/9789* (2017.08); *A61Q 5/00* (2013.01); *A61Q 5/02* (2013.01); *A61Q 5/04* (2013.01); *A61Q 5/06* (2013.01); *A61Q 5/12* (2013.01); *A61K 2800/42* (2013.01); *A61K 2800/434* (2013.01)

(58) Field of Classification Search
None
See application file for complete search history.

(56) References Cited

U.S. PATENT DOCUMENTS

| | | | |
|---|---|---|---|
| 2009/0041708 A1* | 2/2009 | Molenda ................ | A61K 8/355 424/70.11 |
| 2011/0165104 A1* | 7/2011 | Molenda ................ | A61Q 5/02 424/70.9 |
| 2011/0174329 A1* | 7/2011 | Seng ....................... | A61Q 5/00 132/206 |
| 2016/0271264 A1 | 9/2016 | Sojka et al. | |
| 2016/0287508 A1* | 10/2016 | Zhang ..................... | A61K 8/40 |
| 2017/0027852 A1* | 2/2017 | Sweeney ................. | A61K 8/678 |

FOREIGN PATENT DOCUMENTS

| | | |
|---|---|---|
| WO | 99/13826 A1 | 3/1999 |
| WO | 99/13845 A1 | 3/1999 |
| WO | WO-2014199936 A1 * 12/2014 | ............. A61K 8/898 |

OTHER PUBLICATIONS

Anna Amat et al., "Absorption and Emission of the Apigenin and Luteolin Flavonoids: A TDDFT Investigation", J. Phys. Chem., vol. 113, No. 52, pp. 15118-15126, Dec. 31, 2009.

Yan-Li Zhao et al., "Isolation of Chemical Constituents from the Aerial Parts of and their Antiangiogenic and Antiproliferative Activities", Arch. Pharm. Res., vol. 34., No. 5. pp. 703-707, Jun. 9, 2011.

European Search Report dated Dec. 2, 2016 corresponds to EP application No. 16164498.8.

* cited by examiner

*Primary Examiner* — Jyothsna A Venkat
(74) *Attorney, Agent, or Firm* — Norris McLaughlin, P.A.

(57) ABSTRACT

A cosmetic composition is disclosed comprising a synthetic optical brightener and a naturally-derived optical brightener. Both brightener classes absorb and emit light at different wavelengths and possess in combination a superior effect. The combination enhances color brilliance on keratin fibers under daylight and artificial light conditions.

14 Claims, No Drawings

COSMETIC COMPOSITION COMPRISING TWO OPTICAL BRIGHTENERS, METHOD, USE, AND KIT-OF-PARTS THEREOF

This application claims foreign priority benefit of European Patent Application No. 16194498.8, filed Oct. 19, 2016, the disclosure of which patent application in its entirety is incorporated herein by reference.

The present invention relates to a combination of two optical brighteners with different absorption and emission profiles. The combination of brighteners can be used in various consumer products, in particular in cosmetics, such as shampoos, conditioners, and styling products. A composition, method, use, and kit-of-parts is disclosed which make use of the optical brighteners.

Since human beings started to think about beauty and their outer appearance, healthy and especially shiny and brilliant hair was a sign of well-being, comfort, luxuriousness and wealth. This trend has continued and can still be seen in current market portfolios of hair care producers as more products promise the delivery of enhanced optical properties on keratinous fibers. The most attractive route to enhance the optical properties until now is the use of synthetic materials such as silicones with high refractive index and optical brighteners.

However, the consumers' demand for natural ingredients increases while the performance of the products is to be maintained in comparison to synthetic materials, if not increased at the same time.

Several optical brighteners are known from literature which are employed in the treatment of fibers in either textile, laundry, or cosmetic industry. They often have a characteristic structural element, namely a stilbene structure combined with other aromatic rests. Due to the resulting delocalized electron system spreading from aromatic elements over the double bonds of the stilbene structure, these compounds tend to absorb light below 400 nm and emit at higher wavelengths in the range of 400 nm to 500 nm.

Another natural-based brightener was introduced by Phenbiox Corp., namely hydrolyzed *Verbascum thapsus* flower and/or *Verbascum Thapsus* extract, which has a different light absorption and emission profile. In detail, this brightener has a light absorption maximum in the range of 400 nm to 450 nm and light emission maximums in the range of 450 nm to 700 nm.

Market products comprising hydrolyzed *Verbascum thapsus* flower are available for the cosmetic treatment of skin (Mintel 3490755, 3843191). Moreover, *Verbascum Thapsus* extract is marketed in various cosmetic products for hair (Mintel 2069825, 2536657, 1000867).

Besides the prior art on optical brighteners, consumers of cosmetics desire enhanced hair shine and brilliance under all light conditions. As the known optical brighteners are limited to their spectral properties, they show inadequate performance in an environment with low daylight intensities or under artificial light sources. As a result, consumers are disappointed about their vanishing hair beauty in the absence of sunlight.

Thus, there is a need to improve the cosmetic appearance of hair in terms of shine and brilliance outside of the well sun-lightened environment while providing the environment-conscious consumer with the benefit of using natural ingredients.

The inventors of the present invention unexpectedly found that the combination of two optical brighteners with different spectral properties, namely one with light emission maximums in the range of 400 nm to 500 nm, and one with 450 nm to 700 nm, solves the aforementioned problems while employing a naturally luminescent plant extract.

Therefore, the first object of the present invention is a cosmetic composition for keratin fibers, preferably human keratin fibers, more preferably human hair, comprising two or more optical brighteners characterized in that at least one optical brightener is selected from compounds having a light absorption maximum below or equal to 400 nm and a light emission maximum in the range of 400 nm to 500 nm, and at least one optical brightener is selected from naturally-derived compounds having a light absorption maximum in the range of 400 nm and 450 nm and a light emission maximum in the range of 450 nm and 700 nm.

The second object of the present invention is a use of the composition as defined above to confer shine, luster, and color brilliance to keratin fibers, preferably human keratin fibers, more preferably human hair.

The third object of the present invention is a method of conferring shine, luster, and color brilliance to keratin fibers, preferably human keratin fibers, more preferably human hair, comprising the steps of:

a) applying to keratin fibers the composition as defined above, during, or after washing,
b) massaging the composition into the keratin fibers for a time period of 10 s to 600 s,
c) optionally rinsing off the composition,
d) optionally drying the hair.

The fourth object of the present invention is kit-of-parts comprising the composition as defined above, a conditioning composition for keratin fibers and/or a blow dryer.

The term 'optical brightener' within the meaning of the present invention defines compounds or extracts which are luminiscently active. Consequently these compounds or extracts absorb light at a lower wavelength and emit at a higher wavelength. The term 'optical' also defines the inherent function of the compound, namely enhancing the optical appearance of subject matter.

The first optical brightener selected from compounds having a light absorption maximum below or equal to 400 nm and a light emission maximum in the range of 400 nm to 500 nm is according to the general structure of

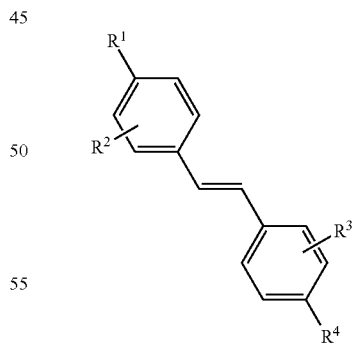

Wherein $R^1$ is selected from H, $C_1$-$C_6$ alkyl, $NH_2$, $SO_3H$, Cl, Br, I,

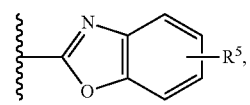

-continued

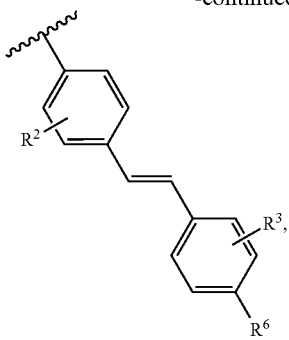

$R^{2-6}$ are independently selected from the list of $R^1$, wherein $R^{1-6}$, may or may not be equal, and wherein the configuration at the double bond may be E or Z, and or its salts.

Suitable compounds according to this definition are

Formula I

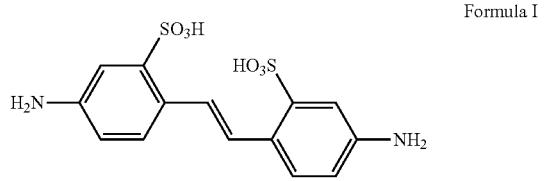 [SMILES: Nc1ccc(/C=C/c2ccc(N)cc2S(=O)(=O)O)c(S(=O)(=O)O)c1]

4,4'-Diamino-2,2'-stilbenedisulfonic acid,

Formula II

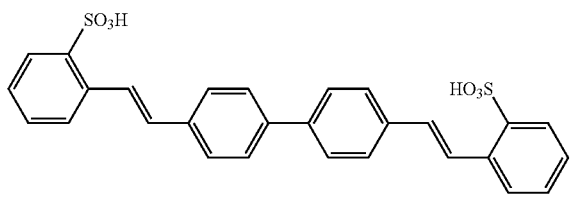

2,2'-([1,1-Biphenyl]-4,4'-diyldi-2,1-ethenediyl)-bis-[benzenesulfonic acid],

Formula III

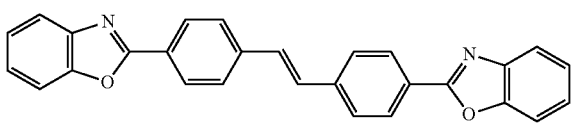

4,4'-Bis-(2-benzoxazolyl)-stilbene,

Formula IV

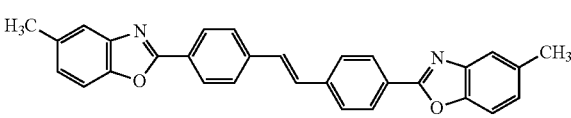

4,4'-Bis-(5-methyl-2-benzoxazolyl)-stilbene.

The preferred first optical brightener selected from compounds having a light absorption maximum below or equal to 400 nm and a light emission maximum in the range of 400 nm to 500 nm is the compound according to Formula II and/or its salts which is marketed as Tinopal CBS-X by BASF Corp.

The concentration of the first optical brightener is in the range of 0.001% to 1% by weight, preferably 0.01% to 1% by weight, and more preferably 0.01% to 0.5% by weight, calculated to the total of the composition.

The second optical brightener selected from naturally-derived compounds having a light absorption maximum in the range of 400 nm and 450 nm and a light emission maximum in the range of 450 nm and 700 nm is an extract of *Verbascum* ssp.

The term '*Verbascum* ssp' according to the present invention is to be understood as the genus of plants which are commonly known under the name 'mullein' and encompasses a variety of subspecies [ssp].

Suitable examples of this genus are *Verbascum thapsus*, *V. virgatum*, *V. phoeniceum*, *V. speciosum*, *V. densiflorum*, and *V. bugulifolium*.

The preferred plant which is used to derive the luminescent extract from is *V. thapsus*.

Such extracts are known under the CTFA name 'hydrolyzed *Verbascum thapsus* flower' and/or '*Verbascum Thapsus* extract' and marketed under the tradename Luminescine by Phenbiox Corp. The aforementioned extract is the most preferred embodiment of the naturally-derived optical brightener.

The preferred combination of optical brighteners according to the present invention is Tinopal CBS-X by BASF Corp. and Luminescine by Phenbiox Corp.

The concentration of the second optical brightener is in the range of 0.001% to 1% by weight, preferably 0.01% to 0.5% by weight, and more preferably 0.01% to 0.1% by weight, calculated as dry matter to the total of the composition.

The weight ratio of first optical brightener to second optical brightener (dry matter) is in the range from 1 to 10,000, preferably from 1 to 1,000, more preferably from 1 to 100, calculated to the total of the composition.

The composition comprising both optical brighteners may be in the form of a cleansing composition (e.g. shampoo), a conditioning composition, a cleansing conditioning composition, and/or a styling composition. It may as well be a leave-in composition and/or a wash-out composition. It is to be noted that the aforementioned list is not comprehensive and that the skilled reader may imagine other applications which are encompassed by the present invention.

The composition may comprise cationic, anionic, zwitterionic, amphoteric, and/or non-ionic surfactants. In a preferred embodiment of the present invention, the composition comprises two anionic surfactants, and one amphoteric surfactant.

Suitable first anionic surfactants are selected from compounds according to the structure Formula V

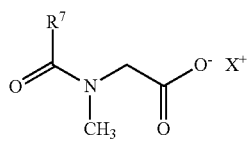

wherein $R^7$ is a straight or branched, substituted or unsubstituted, saturated or unsaturated alkyl chain with a carbon number of $C_9$ to $C_{21}$, preferably $R^7$ is a straight alkyl chain with a carbon number of $C_9$ to $C_{17}$, and $X^+$ is a cation selected from sodium, potassium, magnesium and ammonium ions, which are compounds based on the amino acid sarcosin which are commonly known as sarcosinates.

Suitable compounds are, for example, cocoyl sarcosinate and its salts, lauroyl sarcosinate and its salts, myristoyl sarcosinate and its salts, stearoyl sarcosinate and its salts, oleoyl sarcosinate and its salts, palmitoyl sarcosinate and its salts. Salts are formed with cations selected from sodium, potassium, magnesium, and ammonium ions.

The preferred first surfactant according to the structure of formula V is sodium lauroyl sarcosinate.

The total concentration of the surfactant according to formula V is in the range of 0.1% to 3.5% by weight, preferably 0.2% to 3.5% by weight, more preferably 0.5% to 3.5% by weight, calculated to the total of the composition.

Suitable second anionic surfactants are alkyl sulfate or preferably ethoxylated alkyl ether sulfate surfactant or mixtures thereof with an alkyl chain length of $C_{10}$ to $C_{22}$.

Suitable surfactants are laureth sulfates, coceth sulfate, pareth sulfate, capryleth sulphate, myreth sulfate, oleth sulfate, deceth sulfate, trideceth sulfate, coco sulphate, $C_{10}$-$C_{16}$ alkyl sulphate, $C_{11}$-$C_{15}$ alkyl sulphate, $C_{12}$-$C_{18}$ alkyl sulphate, $C_{12}$-$C_{15}$ alkyl sulphate, $C_{12}$-$C_{16}$ alkyl sulphate, $C_{12}$-$C_{13}$ alkyl sulfate, lauryl sulphate, myrystyl sulphate, palm kernel sulphate, cetearyl sulfate, cetyl sulphate, decyl sulphate, oleyl sulphate, behenyl sulphate and/or their salts. All of the aforementioned anionic surfactants may or may not be ethoxylated at various degrees.

Cations for the surfactants may be selected from sodium, potassium, magnesium and/or ammonium.

The preferred second anionic surfactant is sodium laureth sulfate with 1-5 ethylene oxide units.

The composition may comprise the second anionic surfactant at a total concentration in the range of 5% to 12.5% by weight, calculated to the total of the composition.

The amphoteric surfactant is selected from compounds according to the general structure(s) VI and/or VII

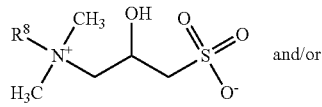

Formula VI and/or

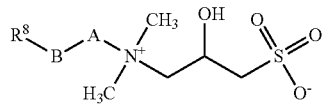

Formula VII wherein $R^8$ is a straight or branched, saturated or unsaturated, substituted or unsubstituted alkyl chain with a carbon number of $C_{10}$ to $C_{22}$, preferably $R^8$ is a straight alkyl chain with a carbon number of $C_{10}$ to $C_{16}$, A is a straight alkyl chain with a carbon number of $C_1$ to $C_6$ or a branched alkyl chain with a carbon number of $C_3$ to $C_6$, preferably A is a linear alkyl chain with a carbon number of $C_3$, and B is an amide or an ester group.

Suitable compounds are known as hydroxysultain surfactants, such as cocoamidopropyl hydroxysultaine, laurylamidopropyl hydroxysultaine, erucamidopropyl hydroxysultaine, lauryl hydroxysultaine, and cocoyl hydrodroxysultaine.

The preferred amphoteric surfactant is lauryl hydroxysultaine.

The composition may comprise amphoteric surfactants at a concentration in the range of 0.1% to 2%, preferably 0.25% to 1.75%, more preferably 0.5% to 1.5% by weight, calculated to the total of the composition.

The weight ratio of total anionic surfactant to total amphoteric surfactant in the composition is in the range from 2.55 to 155, preferably from 7.75 to 51, and more preferably from 9 to 25, and wherein the weight ratio of the first anionic surfactant to the second anionic surfactant is in the range of 0.008 to 0.6, preferably 0.02 to 0.6, and more preferably from 0.1 to 0.4.

The weight ratio of second anionic surfactant to amphoteric surfactant is in the range of 2.5 to 125, preferably from 3.0 to 100, more preferably from 3.5 to 50, further more preferably from 4 to 25.

The weight ratio of first anionic surfactant to amphoteric surfactant in the composition is in the range of 0.067 to 30, preferably from 0.13 to 12, more preferably from 0.13 to 4.

In a particular embodiment, the composition comprises as the first anionic surfactant sodium lauroyl sarcosinate, as a second anionic surfactant sodium laureth sulfate with 1-5 ethoxylate units, and as amphoteric surfactant a lauryl hydroxysultaine, and the total concentration of the aforementioned surfactants is in the range from 6% to 17% by weight, preferably from 7% to 17% by weight, more preferably from 8% to 17% by weight, calculated to the total of the composition.

In a further preferred embodiment, the composition comprises a compound according to the general structure

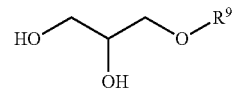

Formula VIII wherein $R^9$ is a linear or branched alkyl chain with a total carbon number of $C_3$ to $C_{12}$, preferably $C_3$ to $C_8$, more preferably $R^9$ is a branched alkyl chain with a total carbon number of $C_8$.

Suitable compounds are propyl glycerine, butyl glycerine, pentyl glycerine, hexyl glycerine, heptyl glycerine, octyl glycerine, nonyl glycerine, decyl glycerine, undecyl glycerine, dodecyl glycrin, ethylhexyl glycerine.

The preferred compound is ethylhexyl glycerine.

The composition comprises the compound according to Formula VIII at a concentration in the range of 0.1% to 1% by weight, preferably from 0.2% to 1% by weight, more preferably from 0.25% to 1% by weight, calculated to the total of the composition.

The weight ratio of total surfactant to amphoteric surfactant is in the range of 1 to 20, preferably 2 to 18, more preferably 3 to 15.

In the most preferred embodiment, the first anionic surfactant is sodium laureth sulfate with 1-5 ethoxylate units, the second anionic surfactant is sodium lauroyl sarcosinate, the amphoteric surfactant is sodium lauryl hydroxysultaine, and the composition further comprises ethylhexyl glycerin.

The composition may further comprise cationic surfactants of quaternary ammonium structure according to

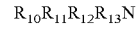

wherein $R_{10}$ is an alky chain having C length of 8 to 30 which may be saturated or unsaturated, straight or branched, $R_{11}$ is an alkyl chain having C length of 1 to 30 which may be saturated or unsaturated, straight or branched, $R_{10}$ and $R_{11}$ additionally may take the structures of $$R_{14}C(O)O(CH_2)_{n1} \text{ or } R_{14}C(O)NH(CH_2)_{n1}$$

wherein $R_{14}$ is an alkyl chain with a C length of 7 to 29 which may be saturated or unsaturated, straight or branched and n1 is a number between 1 and 4, $R_{12}$ and $R_{13}$ are same or the different alkyl chain with a C length of 1 to 4 which may be straight or branched (only for $C_3$ and $C_4$), wherein all alkyl chains may comprise one or more substituents such as hydroxyl- or (poly)-ethoxy groups.

The concentration of cationic surfactants is in the range of 0.1% to 10% by weight, preferably 0.5% to 7.5% by weight, more preferably 1% to 5% by weight, calculated to the total of the composition.

Anions for the cationic surfactants may be selected from chloride, sulfate, or nitrate.

The composition may further comprise linear and/or cyclic silicones and/or siliconols.

Suitable silicones and/or siliconols are dimethicone, dimethiconol, polydimethylsiloxane (DC fluid ranges from Dow Corning), arylated silicones such as phenyl methicone, phenyl trimethicone, diphenyl dimethicone, diphenylsiloxy phenyl trimethicone, tetramethyl tetraphenyl trisiloxane, triphenyl trimethicone, and trimethyl pentaphenyl trisiloxane, aqueous emulsion sof divinyldimethicone/dimethicone copolymer, preferably with a viscosity of higher than $1\times10^8$ mm$^2$/s, more preferably higher than $1.1\times10^8$ mm$^2$/s measured at 0.01 Hz and at approximately 25° C.

The concentration of silicones and/or siliconols is in the range from 0.1% to 30% by weight, preferably from 0.5% to 25% by weight, calculated to the total of the composition.

The composition may further comprise aminosilicone(s), preferably selected from
a. a compound according to the general structure

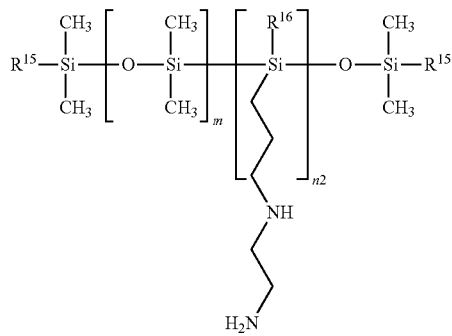

Wherein $R^{15}$ is selected from OH, OCH$_3$, and/or O—Si—(CH$_3$)$_3$, $R^{16}$ is selected from CH$_3$, OCH$_3$, O—(Si—(CH$_3$)$_2$)x-$R^{12}$, and/or O—Si—(CH$_3$)$_3$, with the provision that if $R^{15}$ or $R^{16}$ are selected from O—Si—(CH$_3$)$_3$, then all other $R^{15}$ or $R^{16}$ are selected from O—Si—(CH$_3$)$_3$ and/or OCH$_3$. M and n2 are numbers independently of each other and in the range of 1 to 200. Special reference is made to the aminosilicones sold by Wacker Corporation under the trade name Belsil ADM 652 and Belsil ADM 653, and the ones sold by Shin-Etsu Corp. under the trade name X-52-2265.
b. silicone graft copolymer comprising an organopolysiloxane segment as a main chain thereof and an unsaturated monomer-derived polymer segment as a side chain thereof, which is obtainable by firstly reacting an aminopropyl dimethicone with the thiolactone of acetyl homocysteine and then graft copolymerizing the thus obtained mercapto modified dimethicone with a mixture of N,Ndimethylacrylamide and N-t-butylacrylamide. Such a polymer is known under the CTFA name Polysilicone 28 and marketed by Kao Corporation.
c. an organopolysiloxane, wherein at least two silicon atoms in an organopolysiloxane segments constituting a main chain of the organopolysiloxane are bound to poly(N-acyl-alkyleneimine) segments consisting of repeating units represented by the following general formula via alkylene group containing hetero atom:

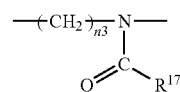

wherein $R^{17}$ is a hydrogen atom, an alkyl group having 1 to 22 carbon atoms, an aralkyl group, or an aryl group; and n3 is 2 or 3; wherein the number-average molecular weight of the poly-(N-acylalkyleneimine) segment is from 1,200 to 5,500, wherein the weight ratio of the organopolysiloxane segments (a) constituting the main chain to the poly-(N-acylalkyleneimine) segments (b) i.e., a/b is from 35/65 to 60/40, wherein the weight-average molecular weight of the adjacent poly-(N-acylalkyleneimine) segments is from 1,300 to 5,500, and wherein the weight-average molecular weight of the organopolysiloxane segment constituting the main chain is from 7,000 to 100,000. Such a polymer is known under the CTFA name Polysilicone 9 and marketed by Kao Corporation. Derivatives of this polymer are disclosed in EP2502615 which is referenced herein.

The total concentration of silicone compounds is in the range from 0.1% to 5% by weight, preferably from 0.2% to 4% by weight, and more preferably from 0.25% to 2.5% by weight, calculated to the total of the composition.

The composition may comprise foaming non-ionic surfactant(s) which is/are different from the compound(s) according to Formula VIII, at a concentration from 0.01% to 2% by weight, preferably from 0.1% to 1.5% by weight, more preferably from 0.25% to 1% by weight, calculated to the total of the composition.

Suitable non-ionic surfactants are in general all commonly known non-ionic surfactants available on the market.

Suitable examples for non-ionic surfactants are fatty alcohol ethoxylates of the following general structure $$R^{18}(OCH_2CH_2)_{n4}OH$$

wherein $R^{18}$ is straight or branched, saturated or unsaturated alkyl chain which may be synthetic or natural with a C chain length in the range of 8 to 40, preferably 9 to 30 and more preferably 9 to 24 and n4 is a number in the range of 5 to 40, preferably 9 to 30.

Non-limiting suitable examples of the fatty alcohol ethoxylates are C9-11 Pareth-6, C9-11 Pareth-8, C9-15 Pareth-8, C11-13 Pareth-9, C11-13 Pareth-10, C11-15 Pareth-5, C11-15 Pareth-7, C11-15 Pareth-9, C11-15 Pareth-12, C11-15 Pareth-15, C11-15 Pareth-20, C11-15 Pareth-30, C11-15 Pareth-40, C11-21 Pareth-10, C12-13 Pareth-5, C12-13 Pareth-6, C12-13 Pareth-7, C12-13 Pareth-9, C12-13 Pareth-10, C12-13 Pareth-15, C12-13 Pareth-23, C12-14 Pareth-5, C12-14 Pareth-7, C12-14 Pareth-9, C12-14 Pareth-11, C12-14 Pareth-12, C12-15 Pareth-5, C12-15 Pareth-7, C12-15 Pareth-9, C12-15 Pareth-10, C12-15 Pareth-11, C12-15 Pareth-12, C12-16 Pareth-5, C12-16 Pareth-7, C12-16 Pareth-9, C13-15 Pareth-21, C14-15 Pareth-7, C14-15 Pareth-8, C14-15 Pareth-11, C14-15 Pareth-12, C14-15

Pareth-13, C20-22 Pareth-30, C20-40 Pareth-10, C20-40 Pareth-24, C20-40 Pareth-40, C20-40 Pareth-95, C22-24 Pareth-33, Beheneth-5, Beheneth-10, Beheneth-15, Beheneth-20, Beheneth-25, Beheneth-30, Ceteareth-5, Ceteareth-6, Ceteareth-7, Ceteareth-10, Ceteareth-11, Ceteareth-12, Ceteareth-15, Ceteareth-20, Ceteareth-25, Ceteareth-30, Ceteareth-35, Ceteareth-40, Laureth-5, Laureth-10, Laureth-15, Laureth-20, Laureth-25, Laureth-30, Laureth-40, Myreth-5, Myreth-10, Ceteth-5, Ceteth-10, Ceteth-15, Ceteth-20, Ceteth-25, Ceteth-30, Ceteth-40, Oleth-5, Oleth-10, Oleth-15, Oleth-20, Oleth-25, Oleth-30, Oleth-40, Steareth-5, Steareth-10, Steareth-15, Steareth-20, Steareth-25, Steareth-30, Steareth-35, and Steareth-40. They may also be comprised in the compositions as a mixture of more than one surfactant.

Further suitable nonionic surfactants are polypropylene glycol ethers of fatty alcohol according to general structure $$R^{19}(OCH_2(CH_3)CH_2)_{n5}OH$$

wherein $R^{19}$ is straight or branched, saturated or unsaturated fatty alcohol which may be synthetic or natural with a C chain length in the range of 8 to 40, preferably 9 to 30 and more preferably 9 to 24 and n5 is a number in the range of 1 to 40, preferably 3 to 30.

Suitable non-limiting examples are PPG-3 Caprylyl ether, PPG-5 Caprylyl ether, PPG-10 Caprylyl ether, PPG-10 Cetyl ether, PPG-20 Cetyl ether, PPG-28 Cetyl ether, PPG-30 Cetyl ether, PPG-7 Lauryl ether, PPG-10 Lauryl ether, PPG-10 Oleyl ether, PPG-20 Oleyl ether, PPG-23 Oleyl ether, PPG-30 Oleyl ether, PPG-11 Sterlyl ether and PPG-15 Stearyl ether.

Further suitable nonionic surfactants are polyethylene glycol fatty acid esters of the following general structure $$R^{20}C(O)(OCH_2CH_2)_{n6}OH$$

wherein $R^{20}$ is straight or branched, saturated or unsaturated alkyl group which may be synthetic or natural with a C chain length in the range of 7 to 39, preferably 9 to 29 and more preferably 9 to 23 and n6 is a number in the range of 5 to 40, preferably 9 to 30.

Suitable non-limiting examples are PEG-8 Behenate, PEG-8 Caprate, PEG-8 Caprylate, PEG-5 Cocoate, PEG-8 Cocoate, PEG-9 Cocoate, PEG-10 Cocoate, PEG-15 Cocoate, PEG-6 Isopalmitate, PEG-6 Isostearate, PEG-8 Isostearate, PEG-9 Isostearate, PEG-10 Isostearate, PEG-12 Isostearate, PEG-20 Isostearate, PEG-30 Isostearate, PEG-40 Isostearate, PEG-6 Laurate, PEG-8 Laurate, PEG-9 Laurate, PEG-10 Laurate, PEG-12 Laurate, PEG-14 Laurate, PEG-20 Laurate, PEG-30 Laurate, PEG-8 Myristate, PEG-20 Myristate, PEG-5 Oleate, PEG-6 Oleate, PEG-7 Oleate, PEG-8 Oleate, PEG-9 Oleate, PEG-10 Oleate, PEG-11 Oleate, PEG-12 Oleate, PEG-15 Oleate, PEG-20 Oleate, PEG-30 Oleate, PEG-32 Oleate, PEG-6 Palmitate, PEG-18 Palmitate, PEG-20 Palmitate, PEG-5 Stearate, PEG-6 Stearate, PEG-7 Stearate, PEG-8 Stearate, PEG-9 Stearate, PEG-10 Stearate, PEG-12 Stearate, PEG-14 Stearate, PEG-15 Stearate, PEG-20 Stearate, PEG-25 Stearate, PEG-30 Stearate, PEG-35 Stearate and PEG-40 Stearate.

Further suitable nonionic surfactants are polypropylene glycol fatty acid esters of the following general structure $$R^{21}C(O)(OCH_2(CH_3)CH_2)_{n8}OH$$

wherein $R^{21}$ is straight or branched, saturated or unsaturated alkyl group which may be synthetic or natural with a C chain length in the range of 7 to 39, preferably 9 to 29 and more preferably 9 to 23 and n8 is a number in the range of 1 to 40, preferably 9 to 30.

Suitable non-limiting examples are PPG-15 Isostearate, PPG-9 Laurate, PPG-26 Oleate and PPG-36 Oleate.

Further nonionic suitable surfactants are polyethylene glycol and polypropylene glycol ether of fatty alcohols of the following general structure $$R^{22}(OCH_2(CH_3)CH_2)_{n6}(OCH_2CH_2)_{n10}OH$$

wherein $R^{22}$ is straight or branched, saturated or unsaturated alkyl group which may be synthetic or natural with a C chain length in the range of 7 to 39, preferably 9 to 29 and more preferably 9 to 23 and n9 and n10 may be the same or different and are a number in the range of 1 to 40.

Suitable non-limiting examples are PPG-2 Ceteareth-9, PPG-4 Ceteareth-12, PPG-4 Ceteareth-20, PPG-2 C9-11 Pareth-5, PPG-2 C9-11 Pareth-7, PPG-2 C9-11 Pareth-8, PPG-2 C9-11 Pareth-11, PPG-2 C12-13 Pareth-8, PPG-2 C12-15 Pareth-6, PPG-4 C 13-15 Pareth-15, PPG-5 C9-15 Pareth-6, PPG-6 C9-11 Pareth-5, PPG-6 C12-15 Pareth-12, PPG-6 C12-18 Pareth-11, PPG-1 Deceth-4, PPG-1 Deceth-5, PPG-1 Deceth-6, PPG-1 Deceth-7, PPG-2 Deceth-3, PPG-2 Deceth-7, PPG-2 Deceth-8, PPG-2 Deceth-10, PPG-2 Deceth-15, PPG-2 Deceth-20, PPG-2 Deceth-30, PPG-2 Deceth-40, PPG-4 Deceth-4, PPG-4 Deceth-6, PPG-4 Deceth-6, PPG-6 Deceth-4, PPG-6 Deceth-9, PPG-8 Deceth-6, PPG-14 Deceth-6, PPG-2 Laureth-5, PPG-2 Laureth-8, PPG-2 Laureth-12, PPG-3 Laureth-8, PPG-3 Laureth-9, PPG-3 Laureth-10, PPG-3 Laureth-12, PPG-4 Laureth-2, PPG-4 Laureth-5, PPG-4 Laureth-7, PPG-4 Laureth-15, PPG-5 Laureth-5, PPG-5 Laureth-3, PPG-20 Laureth-12, PPG-25 Laureth-25, PPG-3 Myreth-3, PPG-3 Myreth-11, PPG-9 Steareth-3, PPG-23 Steareth-34, PPG-30 Steareth-4, PPG-34 Steareth-3, and PPG-38 Steareth-6.

Further suitable nonionic surfactants are ethoxylated triglycerides. Well known and commonly used examples are ethoxylated castor oil such as PEG-40 hydrogenated castor oil or and PEG-60 hydrogenated castor oil.

Further suitable nonionic surfactants are alkyl polyglycosides with the general structure:

$$R^{23}O(R^{24}O)_tZ_x$$

Wherein Z denotes a reducing carbohydrate with $C_5$ to $C_6$, $R^{23}$ is an alkyl group with $C_8$ to $C_{18}$, $R^{24}$ is ethyl or propyl, t ranges from 0 to 10, and x ranges from 1 to 5. Suitable compounds according to this structure are $C_9$-$C_{11}$ alkylpolyglycoside, the structures disclosed in EP-A 70 074, and JP 2015-123019A.

The composition may comprise one or more inorganic, monovalent salt(s) as a first thickening agent wherein the preferred salt is sodium chloride, and PEGylated or non-PEGylated esters of $C_{12}$ to $C_{18}$ fatty acids with pentaerythritol as a second thickening agent.

The viscosity of the composition of the present invention may be adjusted by thickening agents and should not exceed more than 30,000 mPas at 20° C. measured with Brookfield Rheometer at a shear rate of 5 sec$^{-1}$. Preferably the viscosity of the composition is in the range of 5,000 mPas to 25,000 mPas, more preferably 5,000 mPas to 20,000 mPas, each measured at 20° C. with Brookfield Rheometer at a shear rate of 5 sec$^{-1}$.

The composition comprises inorganic, monovalent salt(s) at a concentration in the range from 0.1% to 3.0% by weight, preferably from 0.2% to 2.5% by weight, more preferably from 0.5% to 2.0% by weight, calculated to the total of the composition.

The second thickening agent is PEGylated or non-PEGylated esters of $C_{12}$ to $C_{18}$ fatty acids with pentaerythritol. The preferred compound is PEG-150 pentaerythrityl tetrastearate.

Further suitable thickening agents may be nonionic thickening polymers. Suitable non-limiting examples are cellulose derivatives such as hydroxyethyl cellulose, methyl cellulose, hydroxymethyl cellulose, hydroxypropyl cellulose, guar gum and its derivatives, and konjac mannan and derivatives. Such Thickeners may be included at a concentration of 0.05 to 2.5% by weight calculated to total composition. Concentration of thickener is very much dependent on the thickener itself and also the preparation such as pH value of the composition etc. and therefore should be selected depending on the desired viscosity of the composition.

The composition of the present invention is transparent when being judged with the naked eye by an observer through a layer thickness of 1 cm. However, the composition may be colored with dyestuffs.

The composition according to the present invention may comprise dyestuffs wherein the dyestuffs are selected from non-ionic, nitro, cationic and/or anionic direct dyes.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18, and HC Yellow 16.

Suitable cationic dyes are in principle those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87, HC Blue 17 and Basic Orange 31. The most preferred ones are Basic red 51, Basic Yellow 87 and Basic Orange 31 sold by BASF, HC Blue 17, Basic Blue 124.

Suitable neutral dyes including nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HO Yellow No. 10, HO Yellow No. 11, HO Yellow No. 12, HO Yellow No. 13, HO Yellow No. 14, HO Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

The composition may comprise one or more hair direct dye at a total concentration of 0.001% to 10% by weight, preferably 0.005% to 7.5% by weight, and more preferably 0.01% to 5% by weight, calculated to the total of the composition. The composition can also comprise a mixture of several direct dyes, i.e., an anionic, a cationic and/or nonionic ones. In such a case the dyes may be mixed at any ratio with each other.

The pH of the compositions according to the present invention is suitably between 3.0 and 8.0 and preferably in the range of 3.5 to 6.5, more preferably 4.5 to 6.0 and most preferably 4.5 to 5.5.

In principle, the pH of the composition can be adjusted with any organic and/or inorganic acid(s) or base or their mixtures. Suitable acids are phosphoric acid, hydrochloric acid as the inorganic ones and to the organic acids the well-known citric acid and lactic acid, glycolic acid, glyoxylic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid. Suitable bases are sodium hydroxide or potassium hydroxide.

The composition of the present invention may additionally comprise any compound customarily found in cleansing compositions such as chelating agents, preservatives and fragrance.

Suitable chelating agents are selected from polycarboxy acids. The preferred one is ethylene diamine tetraacetic acid, i.e. EDTA. A typical useful concentration range for chelating agents is 0.01% to 2.5% by weight, calculated to the total composition.

The composition of the present invention may comprise one or more organic solvents. Suitable organic solvents are ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, butylene glycol, ethylenecarbonate, propyleneglycol, poypropyleneglycols, ethyleneglycol monoethylether, ethylene glycol monobutyl ether, ethylene glycol monophenyl ether, 1-phenylethylalcohol, 2-phenylethylalcohol, o-methoxyphenol.

The most preferred ones are butylene glycol, ethanol, isopropanol, benzylalcohol and polypropylene glycols.

The concentration of organic solvents should not exceed 10%, and preferably range from 0.1% to 7.5% by weight, more preferably from 0.1% to 5% by weight, calculated to the total of the composition.

The skilled in the art will recognize that the majority of the aforementioned organic solvents may act as preservatives as well. However, the composition of the present invention may comprise any other known preservative or preservative mixture besides and/or including organic solvents.

The composition of the present invention may further comprise cationic conditioning polymers. Suitable cationic polymers are those of best known with their INCI category name Polyquaternium.

Typical examples of those are Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium 49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87 as well as silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20, silicone quaternium-21 and silicone quaternium-22.

As well those polymers known with their INCI category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

It has further been found out that especially those of cationic cellulose type polymers known as Polymer JR type from Amerchol such as Polyquaternium 10 or cationic galactomannans such as cationic guar gum known with trade name Jaguar from Rhône-Poulenc which are chemically for example Guar hydroxypropyl trimonium chloride and cationic Lara gum and its derivatives known with INCI name *Caesalpinia spinosa* hydroxypropyltrimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, cationic *Caesalpinia spinosa* gum derivatives, polyquaternium 6, polyquaternium 7, polyquaternium 67 and polyquaternium 70.

The cationic polymers also include the quaternized products of graft polymers from organopolysiloxanes and polyethyl oxazolines described in EP-A 524 612 and EP-A 640 643.

Compositions comprise cationic polymer at a concentration of 0.01 to 5%, preferably 0.02 to 4%, more preferably 0.05 to 3% and most preferably 0.1 to 2.5% by weight, calculated to the total of the composition.

The composition of the present invention may further comprise one or more UV filters which may be selected from water soluble ones as well as oils soluble ones. The oil soluble UV filter are more preferred ones as they show no interaction with the cationic quaternary ammonium polymers. Non-limiting examples are 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof, 3-(4'-methyl benzylidene)-DL-campher, and/or polysilicone-15.

The total UV filter concentration may be in the range of 0.01% to 1% by weight, calculated to the total composition.

In a further embodiment of the present invention, the composition may comprise one or more ubiquinone derivatives of the following general structure

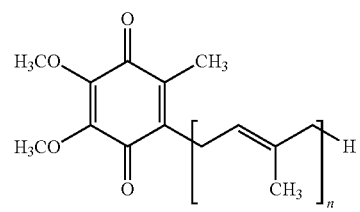

where n is a number between 1 and 10. It should be noted that the compositions of the present invention can certainly comprise more than one ubiquinone. Preferred ubiquinones are the ones where n is a number between 6 and 10 and especially preferred is Ubiquinone 50 where n is 10, also known as Coenzyme Q10.

The composition may further comprise one or more amino acid(s). Suitable amino acids may be all of the known amino acids such as arginine, alanine, asparagine, glutamine, glycine, histidine, leucine, lysine, methionine, phenylalanine, proline, serine, threonine, tryptophan, tyrosine and valine.

The concentration of amino acids may be in the range of 0.01% to 5% by weight, preferably 0.1% to 3% by weight, and more preferably 0.2% to 2.5% by weight, and most preferably 0.25% to 2% by weight, calculated to the total of the composition.

The composition of the present invention may further comprise any known vitamin and/or antioxidant.

The following examples are to illustrate the present invention, but not to limit it.

EXAMPLES

Example 1

The following cleansing compositions were prepared by conventional formulation techniques:

| INCI | Comparative 1 [by weight] | Comparative 2 [by weight] | Inventive [by weight] |
| --- | --- | --- | --- |
| Sodium Laureth Sulfate | 10.0% | 10.0% | 10.0% |
| Sodium Lauroyl Sarcosinate | 3.0% | 3.0% | 3.0% |
| Lauryl Hydroxysultaine | 1.0% | 1.0% | 1.0% |
| Disodium Distyrylbiphenyl disulfonate* | — | 0.01% | 0.01% |
| Hydrolyzed *Verbascum Thapsus* Extract** | 0.5% | — | 0.49% |
| Water | | | Ad 100.0% |

*Tinopal CBS-X by BASF Corp.
**Luminescine by PhenBiox Corp.

The pH of all of the compositions was adjusted to 5.5 with HCl/NaOH.

Caucasian hair streaks were obtained from Fischbach+ Miller Haar, Laupheim, Germany, having a length of about 21 cm. The hair streaks were equally colored with oxidative hair color marketed under the tradename Goldwell Topchic. Upon washing with a commercial shampoo marketed under the tradename Goldwell Dualsenses Deep Cleansing Shampoo, the hair streaks were air dried. 2 g of the above compositions were applied onto the pre-colored hair streaks and each streak was massaged for 60 s. The hair streaks were then rinsed-off with water and blow-dried with a conventional blow-drier.

The treated hair streaks were evaluated by a panel of 10 trained experts under two different light conditions: 1) under day-light conditions, and 2) under an artificial light source which is common in office buildings. As artificial light source a fluorescent lamp marketed under the trade name Lumilux Cool White by Osram Corp. was selected. The trained experts did not receive information in the treatment groups prior to their evaluation. The experts were asked to judge color brilliance. They were given a scale from 1 to 10 wherein 1 is a rating for poor performance and 10 is a rating for excellent performance. Judgement was performed against untreated streaks.

| Panelist # | Comparative 1 daylight | Comparative 2 daylight | Inventive daylight | Comparative 1 artificial light | Comparative 2 artificial light | Inventive artificial light |
| --- | --- | --- | --- | --- | --- | --- |
| 1 | 4 | 5 | 7 | 6 | 7 | 9 |
| 2 | 3 | 5 | 6 | 7 | 8 | 10 |
| 3 | 5 | 4 | 5 | 5 | 6 | 8 |
| 4 | 3 | 4 | 6 | 5 | 6 | 7 |
| 5 | 4 | 3 | 5 | 6 | 6 | 7 |
| 6 | 4 | 5 | 7 | 6 | 5 | 7 |
| 7 | 6 | 5 | 8 | 7 | 7 | 9 |
| 8 | 6 | 4 | 7 | 5 | 7 | 8 |
| 9 | 3 | 4 | 6 | 5 | 6 | 8 |
| 10 | 5 | 6 | 6 | 7 | 6 | 7 |
| Mean value | 4.3 | 4.5 | 6.3 | 5.9 | 6.4 | 8.0 |
| Standard deviation | 1.16 | 0.85 | 0.95 | 0.88 | 0.84 | 1.05 |

Statistical evaluation of results was performed with one-way ANOVA combined with a Tukey's posthoc test with freely available software.

For the treatment groups under daylight conditions, there was no significant difference found between comparative 1 and comparative 2 ($p>0.1$). However, each comparative example performed significantly worse than the inventive example ($p<0.01$).

For the treatment groups under artificial light conditions, there was also no significant difference found between comparative 1 and 2 ($p>0.1$). Each comparative example performed significantly worse than the inventive example ($p<0.01$).

As a result, the inventive example was superior under daylight and artificial light conditions in terms of color brilliance as shown by superior judgements by experts.

Example 2

The following leave-in treatment for hair was prepared by conventional formulation techniques.

| Ingredients | % by weight |
| --- | --- |
| Trisiloxan | 12.0% |
| Cyclopentasiloxane | 9.0% |
| Dimethiconol | 1.5% |
| Polyquaternium 37 | 1.0% |
| Ethylhexyl glycerine | 0.1% |
| Phenoxyethanol | 0.70% |
| Disodium Distyrylbiphenyl disulfonate* | 0.05% |
| Hydrolyzed *V. thapsus* flower** | 0.25% |
| Water | ad 100.0% |

*Tinopal CBS-X by BASF Corp.
**Luminescine by PhenBiox Corp.

The pH of the above composition was adjusted to 5.0 with HCl/NaOH.

Example 3

The following leave-in treatment for hair was prepared by conventional formulation techniques.

| Ingredients | % by weight |
| --- | --- |
| Trisiloxan | 12.0% |
| Cyclopentasiloxane | 9.0% |
| Dimethiconol | 1.5% |
| Polyquaternium 37 | 1.0% |
| Ethylhexyl glycerine | 0.1% |

-continued

| Ingredients | % by weight |
| --- | --- |
| Phenoxyethanol | 0.70% |
| Disodium Distyrylbiphenyl disulfonate* | 0.05% |
| Hydrolyzed *V. thapsus* flower** | 0.25% |
| Basic Blue 124 | 0.10% |
| Water | ad 100.0% |

*Tinopal CBS-X by BASF Corp.
**Luminescine by PhenBiox Corp.

The pH of the above composition was adjusted to 5.0 with HCl/NaOH.

Example 4

The following cleansing composition was prepared by conventional formulation techniques.

| Ingredients | % by weight |
| --- | --- |
| Sodium laureth sulfate | 12.5 |
| Sodium lauroyl sarcosinate | 1.0 |
| Lauryl hydroxysultaine | 2.0 |
| Ethylhexylglycerin | 1.0 |
| Polyquaternium 10 | 0.5 |
| Amodimethicone microemulsion* | 0.6 |
| Sodium chloride | 2.0 |
| PEG-150 Pentaerythrityl Tetrastearate | 0.25 |
| Trideceth-10 | 0.5 |
| Butylene glycol | 0.25 |
| Disodium Distyrylbiphenyl disulfonate** | 0.05 |
| Hydrolyzed *V. thapsus* extract*** | 0.45 |
| Preservatives | q.s. |
| Water | ad 100 |

*X-52-2265 from Shin-Etsu Corp.
**Tinopal CBS-X from BASF Corp.
***Luminescine from Phenbiox Corp.

Example 5

The following hair conditioning composition was prepared by conventional formulation techniques.

| Ingredients | % by weight |
| --- | --- |
| Cetearyl alcohol | 5.0 |
| Light mineral oil | 2.0 |
| Ceteareth-10 | 0.5 |
| Cetrimonium chloride | 2.0 |
| Quaternium 80 | 2.0 |
| Propylen glycol | 0.5 |
| Phenoxyethanol | 0.70 |
| Disodium Distyrylbiphenyl disulfonate* | 0.05 |
| Hydrolyzed *V. thapsus* flower** | 0.25 |
| Basic Blue 124 | 0.10 |
| Water | ad 100.0 |

*Tinopal CBS-X by BASF Corp.
**Luminescine by PhenBiox Corp.

The pH of the above composition was adjusted to 5.0 with HCl/NaOH.

Example 6

The following hair conditioning composition was prepared by conventional formulation techniques.

| Ingredients | % by weight |
| --- | --- |
| Cetearyl alcohol | 5.0 |
| Light mineral oil | 2.0 |
| Ceteareth-10 | 0.5 |
| Stearamidopropyl dimethylamine | 2.0 |
| Quaternium 80 | 2.0 |
| Polyquaternium 10 | 0.2 |
| Propylene glycol | 0.5 |
| Phenoxyethanol | 0.70 |
| Disodium Distyrylbiphenyl disulfonate* | 0.05 |
| Hydrolyzed *V. thapsus* flower** | 0.25 |
| Basic Blue 124 | 0.10 |
| Water | ad 100.0 |

*Tinopal CBS-X by BASF Corp.
**Luminescine by PhenBiox Corp.

The pH of the above composition was adjusted to 5.0 with HCl/NaOH.

The invention claimed is:

1. A cosmetic composition for keratin fibers, the cosmetic composition comprising:
    two optical brighteners selected from
    a) first optical brightener is

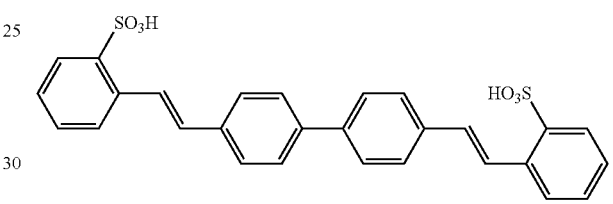

and/or its salts having a light absorption maximum below 400 nm and a light emission maximum of 400 nm to 500 nm, and
    b) second optical brightener is hydrolyzed *Verbascum thapsus* flower and/or *Verbascum thapsus* extract having a light absorption maximum of 400 nm to 450 nm and a light emission maximum of 450 nm to 700 nm, wherein
    a weight ratio of the first optical brightener to the second optical brightener is in a range from 1 to 10,000, calculated as dry matter to a total of the cosmetic composition.

2. The cosmetic composition of claim 1, further comprising cationic surfactants, anionic surfactants, zwitterionic surfactants, amphoteric surfactants, non-ionic surfactants, and/or a mixture of more than one surfactant.

3. The cosmetic composition of claim 1, further comprising a weight ratio of total anionic surfactant to total amphoteric surfactant in a range from 2.55 to 155.

4. The cosmetic composition of claim 1, wherein the cosmetic composition has a pH range of 3.0 to 8.0.

5. The cosmetic composition of claim 1, further comprising linear silicones, cyclic silicones, and/or siliconols.

6. The cosmetic composition of claim 1, further comprising cationic conditioning polymers.

7. The cosmetic composition of claim 1, further comprising:
    a. a compound of a general structure

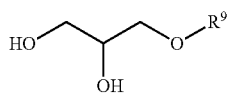

wherein $R^9$ is a linear or branched alkyl chain with a total carbon number of $C_3$ to $C_{12}$.

8. The cosmetic composition of claim 1, further comprising aminosilicone.

9. A method of conferring shine, luster, and color brilliance to keratin fibers, the method comprising:
 a) applying the cosmetic composition of claim 1 to keratin fibers during or after washing,
 b) massaging the cosmetic composition into the keratin fibers for a time period of 10 seconds to 600 seconds,
 c) optionally rinsing the cosmetic composition off the keratin fibers,
 d) optionally drying the keratin fibers.

10. A kit-of-parts comprising:
 the cosmetic composition of claim 1;
 a conditioning composition for keratin fibers; and
 a blow dryer.

11. The cosmetic composition of claim 4, wherein the pH range of the cosmetic composition is 3.5 to 6.5.

12. The cosmetic composition of claim 11, wherein the pH range of the cosmetic composition is 4.5 to 5.5.

13. The cosmetic composition of claim 4, wherein the weight ratio of the first optical brightener to the second optical brightener ranges from 1 to 100, calculated as dry matter to a total of the cosmetic composition.

14. The cosmetic composition of claim 12, wherein the cosmetic composition is in the form of a styling composition.

* * * * *